(12) United States Patent
Park et al.

(10) Patent No.: US 12,026,883 B1
(45) Date of Patent: Jul. 2, 2024

(54) APPARATUS AND METHOD FOR EXTRACTING VASCULAR FUNCTION FROM BRAIN-RELATED INFORMATION

(71) Applicant: Heuron Co., Ltd., Incheon (KR)

(72) Inventors: Gyu Ha Park, Incheon (KR); Dohyun Kim, Suwon-si (KR); Soohwa Song, Incheon (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 18/468,947

(22) Filed: Sep. 18, 2023

(30) Foreign Application Priority Data

Jul. 4, 2023 (KR) .................. 10-2023-0086205

(51) Int. Cl.
*G06T 7/00* (2017.01)
*G06T 7/11* (2017.01)
(Continued)

(52) U.S. Cl.
CPC ............. *G06T 7/0012* (2013.01); *G06T 7/11* (2017.01); *G06T 7/246* (2017.01); *G06T 11/008* (2013.01);
(Continued)

(58) Field of Classification Search
CPC ......... G06T 7/0012; G06T 7/11; G06T 7/246; G06T 11/008; G06T 11/206;
(Continued)

(56) References Cited

U.S. PATENT DOCUMENTS

| 8,837,800 B1 | 9/2014 | Bammer et al. | |
|---|---|---|---|
| 2011/0103665 A1* | 5/2011 | Gulsun | G06T 7/248 382/131 |

(Continued)

FOREIGN PATENT DOCUMENTS

| KR | 10-1540254 B1 | 7/2015 |
|---|---|---|
| KR | 10-1754291 B1 | 7/2017 |

(Continued)

OTHER PUBLICATIONS

Monica et al, (Novel 4D Image Reconstruction for Dynamic X-Ray Computed Tomography in Slow Rotating Scanners, IEEE 2014, 3 Pages) (Year: 2014).*

(Continued)

*Primary Examiner* — Amara Abdi
(74) *Attorney, Agent, or Firm* — Sughrue Mion, PLLC

(57) ABSTRACT

An aspect of the present disclosure provides an apparatus for extracting a vascular function including an information reception unit configured to extract an original CT image from brain-related information received from the outside; an NIFTI image transformation unit configured to transform the original CT image into an NIFTI file format image to acquire time sequence data; a time interpolation unit configured to apply time interpolation to the original CT image through the time sequence data to transform the original CT image into each time-specific 3D CT image; a vessel segmentation unit configured to predict a vessel segmentation mask by passing the each time-specific 3D CT image through a deep learning-based vessel segmentation deep-learning model 141 and generate a 4D vessel mask image by stacking the 3D CT images based on a time axis; and a vascular function extraction unit configured to extract a vascular function from a vessel region of the 4D vessel mask image and calculate a blood flow parameter using an artery function which is one of the vascular functions.

22 Claims, 12 Drawing Sheets

(51) Int. Cl.
  *G06T 7/246* (2017.01)
  *G06T 11/00* (2006.01)
  *G06T 11/20* (2006.01)
  *G16H 30/40* (2018.01)

(52) U.S. Cl.
  CPC .......... *G06T 11/206* (2013.01); *G16H 30/40* (2018.01); *G06T 2200/04* (2013.01); *G06T 2207/10076* (2013.01); *G06T 2207/30016* (2013.01); *G06T 2207/30104* (2013.01); *G06T 2211/441* (2023.08)

(58) Field of Classification Search
  CPC ....... G06T 2200/04; G06T 2207/10076; G06T 2207/30016; G06T 2207/30104; G06T 2211/441; G16H 30/40
  See application file for complete search history.

(56) References Cited

U.S. PATENT DOCUMENTS

| | | | | |
|---|---|---|---|---|
| 2014/0376791 A1* | 12/2014 | Heigl | .................... | G06T 11/008 382/128 |
| 2019/0164649 A1* | 5/2019 | Lavi | ...................... | A61B 5/026 |
| 2020/0113450 A1* | 4/2020 | Nishioka | ................ | G16H 10/60 |
| 2020/0359981 A1* | 11/2020 | Straka | ................... | G16H 50/20 |
| 2022/0148711 A1* | 5/2022 | Kuo | ........................ | G16H 50/70 |
| 2023/0147641 A1* | 5/2023 | Wang | ..................... | G06V 20/40 345/474 |
| 2023/0157650 A1* | 5/2023 | Hofmann | ............. | A61B 6/5288 382/131 |
| 2023/0298180 A1* | 9/2023 | Kweon | .................. | A61B 6/481 382/128 |

FOREIGN PATENT DOCUMENTS

| | | | | |
|---|---|---|---|---|
| KR | 10-1860566 B1 | 5/2018 | | |
| KR | 10-1992057 B1 | 6/2019 | | |
| KR | 10-2058884 B1 | 12/2019 | | |
| KR | 102058884 | * 12/2019 | .............. | A61B 3/14 |
| KR | 10-2068836 B1 | 2/2020 | | |
| WO | 2020/227176 A1 | 11/2020 | | |

OTHER PUBLICATIONS

Korean Patent Office, Notice of Preliminary Rejection issued Sep. 11, 2023 in counterpart KR Application No. 10-2023-0086205, with English translation.

Korean Patent Office, Decision for Grant of Patent issued Nov. 24, 2023 in counterpart KR Application No. 10-2023-0086205, with English translation.

* cited by examiner

APPARATUS AND METHOD FOR EXTRACTING VASCULAR FUNCTION FROM BRAIN-RELATED INFORMATION

CROSS-REFERENCE TO RELATED APPLICATIONS

This application claims the priority of Korean Patent Application No. 10-2023-0086205 filed on Jul. 4, 2023, in the Korean Intellectual Property Office, the disclosure of which is incorporated herein by reference.

BACKGROUND

Field

The present disclosure relates to an apparatus and a method for extracting a vascular function from brain-related information, and more particularly, to an apparatus and a method capable of accurately extracting a vascular function from brain-related information.

Description of the Related Art

In a method for non-invasively measuring a fluid flow in a human body, such as blood flow, a phase-contrast magnetic resonance imaging technique using a magnetic resonance imaging device has been widely used. In the technique, immediately after an R-wave of an electrocardiogram, a reference image that does not reflect a velocity is captured using a gradient field pulse that sets the blood flow velocity image to 0, and a velocity-encoding image in which the blood flow velocity is reflected is captured using a velocity-encoding gradient field. Thereafter, a reference image and a velocity-encoding image are captured. The images are continuously captured in pairs during one cycle of the electrocardiogram, and captured until a k-space is completely filled while changing the size of a phase encoding. Thereafter, the captured image is reconstructed into a velocity image to measure the blood flow velocity during one cycle of the electrocardiogram.

However, the method has been pointed out a problem in that only the blood flow velocity may be known in analyzing the blood flow, and it is insufficient to express high temporal resolution and accurate blood flow.

To this end, in U.S. Pat. No. 8,837,800, etc., for analyzing artery and vein flows, there is disclosed a method of selecting some of pixels configuring an image to derive artery and vein functions using a medical image and deriving an artery function and a vein function for a vessel configured by respective pixels by using generalization and Gaussian transform of signals of the respective pixels.

However, even by these conventional methods, there is a problem in that the artery function and the vein function are not accurately derived and errors occur, and particularly, a problem has been pointed out in that the blood flow is not accurately analyzed from a vessel recognized from a medical image due to an inaccurate artery function.

Accordingly, an object of the present disclosure is to provide a user with an apparatus and a method capable of accurately extracting a vascular function so as to accurately analyze blood flow from a vessel.

Specifically, an object of the present disclosure is to provide a user with an apparatus and a method capable of extracting a vascular function from brain-related information by extracting a vascular function from brain-related information generated based on an original CT image and then correcting an inaccurate artery function to acquire an accurate artery function, in order to accurately calculate blood flow parameters such as cerebral blood flow (CBF), cerebral blood volume (CBV), mean transit time (MTT), etc.

RELATED ART DOCUMENT

Patent Document

Korean Patent Registration No. 10-1992057 (issued on Jun. 24, 2019)
Korean Patent Registration No. 10-1754291 (issued on Jul. 6, 2017)
U.S. Pat. No. 8,837,800 (registered on Sep. 16, 2014)

SUMMARY

An object of the present disclosure is to provide a user with an apparatus and a method for extracting a vascular function from brain-related information.

Specifically, the present disclosure aims to provide a user with an apparatus and a method for extracting a vascular function from brain-related information by extracting a vascular function from brain-related information generated based on an original CT image and then correcting an inaccurate artery function to acquire an accurate artery function, in order to accurately calculate blood flow parameters such as CBV, MTT, and CBF.

Meanwhile, the technical objects to be achieved in the present disclosure are not limited to the aforementioned technical objects, and other technical objects, which are not mentioned above, will be apparently understood to a person having ordinary skill in the art from the following description.

An aspect of the present disclosure provides an apparatus for extracting a vascular function including an information reception unit configured to extract an original CT image from brain-related information received from the outside; an NIFTI image transformation unit configured to transform the original CT image into an NIFTI file format image to acquire time sequence data; a time interpolation unit configured to apply time interpolation to the original CT image through the time sequence data to transform the original CT image into each time-specific 3D CT image; a vessel segmentation unit configured to predict a vessel segmentation mask by passing the each time-specific 3D CT image through a deep learning-based vessel segmentation deep-learning model 141 and generate a 4D vessel mask image by stacking the 3D CT images based on a time axis; and a vascular function extraction unit configured to extract a vascular function from a vessel region of the 4D vessel mask image and calculate blood flow parameter using an artery function which is one of the vascular functions.

The apparatus for extracting the vascular function may further include a motion correction unit configured to correct a motion of the each time-specific 3D CT image based on a rigid transformation, between the predicting of the vessel segmentation mask and the generating of the 4D vessel mask image by the vessel segmentation unit.

The vessel segmentation unit may acquire a vessel segmentation mask of the 4D vessel mask image including at least two or more of a bone mask, a brain mask, a tissue mask, a vein mask, and an artery mask, which are predicted by the vessel segmentation deep-learning model.

The artery mask may be used when the vascular function extraction unit extracts the artery function.

The vein mask may be used when the vascular function extraction unit extracts the vein function.

The vascular function extraction unit may generate a first graph based on the highest intensity value in a time-specific phase corresponding to a pixel point of each vessel corresponding to Slice, Height, and Width coordinates in the vessel region of the 4D vessel mask image.

The vascular function extraction unit may remove spike noise in the process of generating the first graph.

The vascular function extraction unit may generate a second graph by sorting the intensity of the first graph based on the order in which the intensity reaches a peak fastest in the first graph.

The second graph may be a graph of the top 70 to 90% based on the order in which the intensity reaches a peak fastest in the first graph.

The vascular function extraction unit may generate a third graph based on the order of increasing intensity values of peak points from the second graph.

The third graph may be a graph of the top 10 to 20% based on the order of increasing the intensity value of the peak point of the second graph.

The vascular function extraction unit may generate a fourth graph based on the sum of changes in intensity for each time point of the third graph.

The fourth graph may be a graph of the bottom 20 to 40% based on the order of increasing the sum of changes in intensity for each time point of the third graph.

The vascular function extraction unit may calculate an average of intensities based on a time axis in the fourth graph, and generate a fifth graph by assuming points out of a predetermined range as outliers and removing the points.

The fifth graph may be a graph of removing points out of a range of average ±1 to 3σ in the fourth graph as outliers.

The vascular function extraction unit may generate a sixth graph by performing Gaussian fitting on the remaining points of the fifth graph.

The vascular function extraction unit may extract a plurality of graphs having the closest distance to the sixth graph from the fourth graph, simultaneously with the aforementioned Gaussian fitting process, and generate a candidate graph based on the plurality of graphs and the sixth graph.

The candidate graph may be obtained by adding or deleting a graph by a user.

The vascular function extraction unit may extract an artery function-based artery function graph based on the process of generating the candidate graph from the first graph, and the artery function graph may be obtained by correcting the artery function based on the process of adding or deleting the candidate graph.

The vascular function extraction unit may calculate blood flow parameters such as cerebral blood volume (CBV), mean transit time (MTT), and cerebral blood flow (CBF) based on the corrected artery function.

The time interpolation unit may transform the original CT image into each time-specific 3D CT image in units of 1 second by applying time interpolation in units of 1 second to the original CT image.

Another aspect of the present disclosure provides a method for extracting a vascular function including (a) extracting, by an information reception unit, an original CT image from brain-related information received from the outside; (b) transforming, by an NIFTI image transformation unit, the original CT image into an NIFTI file format image to acquire time sequence data; (c) applying, by a time interpolation unit, time interpolation to the original CT image through the time sequence data to transform the original CT image into each time-specific 3D CT image; (d) predicting, by a vessel segmentation unit, a vessel segmentation mask by passing the each time-specific 3D CT image through a deep learning-based vessel segmentation deep-learning model 141 and generating a 4D vessel mask image by stacking the 3D CT images based on a time axis; and (e) extracting, by an vascular function extraction unit, a vascular function from a vessel region of the 4D vessel mask image and calculating blood flow parameter using an artery function which is one of the vascular functions.

According to the present disclosure, it is possible to provide a user with an apparatus and a method for extracting a vascular function from brain-related information.

Specifically, according to the present disclosure, it is possible to provide a user with an apparatus and a method for extracting a vascular function from brain-related information by extracting a vascular function from brain-related information generated based on an original CT image and then correcting an inaccurate artery function to acquire an accurate artery function, in order to accurately calculate blood flow parameters such as CBV, MTT, and CBF.

Meanwhile, effects which can be obtained in the present disclosure are not limited to the aforementioned effects, and other effects, which are not mentioned above, will be apparently understood to a person having ordinary skill in the art from the following description.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Figure 1:
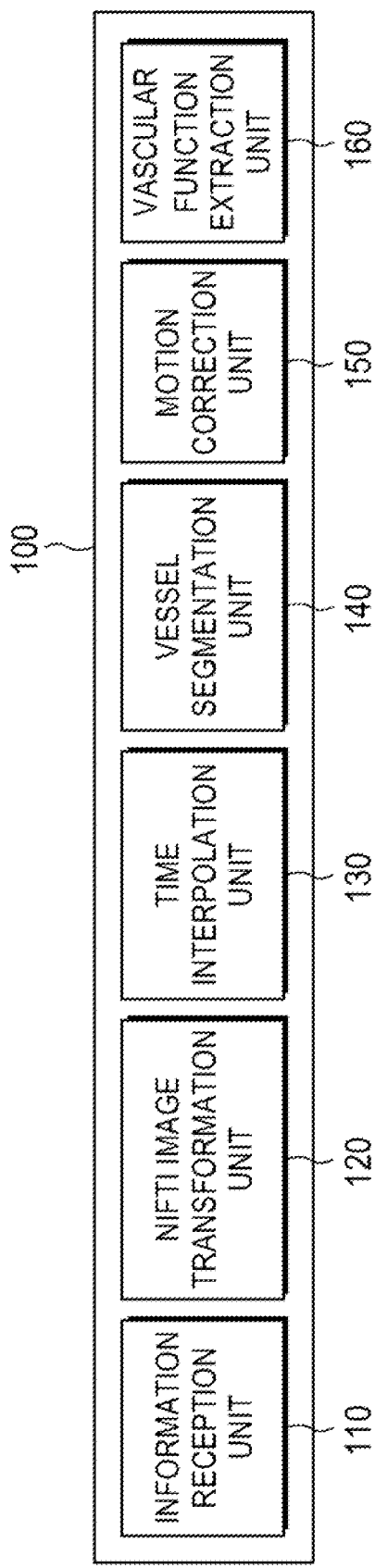
FIG. 1 illustrates an example of a block diagram of an apparatus for extracting a vascular function from brain-related information according to an exemplary embodiment of the present disclosure.

Hereinafter, a preferred exemplary embodiment of the present disclosure will be described with reference to the drawings. In addition, exemplary embodiments to be described below do not unfairly limit the content of the present disclosure described in claims, and the entire configuration described in the exemplary embodiments cannot be essential as a solution to the present disclosure.

Hereinafter, an apparatus and a method according to a preferred exemplary embodiment of the present disclosure will be described in detail with reference to the accompanying drawings.

Problems of Related Art

In a method for non-invasively measuring a fluid flow in a human body, such as blood flow, a phase-contrast magnetic resonance imaging technique using a magnetic resonance imaging device has been widely used. In the technique, immediately after an R-wave of an electrocardiogram, a reference image that does not reflect a velocity is captured using a gradient field pulse that sets the blood flow velocity image to 0, and a velocity-encoding image in which the blood flow velocity is reflected is captured using a velocity-encoding gradient field. Thereafter, a reference image and a velocity-encoding image are captured. The images are continuously captured in pairs during one cycle of the electrocardiogram, and captured until a k-space is completely filled while changing the size of a phase encoding. Thereafter, the captured image is reconstructed into a velocity image to measure the blood flow velocity during one cycle of the electrocardiogram.

However, the method has been pointed out a problem in that only the blood flow velocity may be known in analyzing the blood flow, and it is insufficient to express high temporal resolution and accurate blood flow.

To this end, in U.S. Pat. No. 8,837,800, etc., for analyzing artery and vein flows, there is disclosed a method of selecting some of pixels configuring an image to derive artery and vein functions using a medical image and deriving artery and vein functions for a vessel configured by respective pixels by using generalization and Gaussian transform of signals of the respective pixels.

However, even by these conventional methods, there is a problem in that the artery function and the vein function are not accurately derived and errors occur, and particularly, a problem has been pointed out in that the blood flow is not accurately analyzed from a vessel recognized from a medical image due to an inaccurate artery function.

Accordingly, an object of the present disclosure is to provide a user with an apparatus and a method capable of accurately extracting a vascular function so as to accurately analyze blood flow from a vessel.

Specifically, the present disclosure aims to provide a user with an apparatus and a method for extracting a vascular function from brain-related information by extracting a vascular function from brain-related information generated based on an original CT image and then correcting an inaccurate artery function to acquire an accurate artery function, in order to accurately calculate blood flow parameters such as CBV, MTT, and CBF.

Apparatus and Method for Extracting Vascular Function

A vascular function extraction apparatus 100 accurately extracts a vascular function based on brain-related information generated based on a CT image and a cerebrovascular map, and components for the vascular function extraction apparatus are as illustrated in FIG. 1.

FIG. 1 illustrates an example of a block diagram of an apparatus for extracting a vascular function from brain-related information according to an exemplary embodiment of the present disclosure.

Referring to FIG. 1, the vascular function extraction apparatus 100 proposed in the present disclosure may include an information reception unit 110, an NIFTI image transformation unit 120, a time interpolation unit 130, a vessel segmentation unit 140, a motion correction unit 150, and a vascular function extraction unit 160 in order to extract a vascular function.

In the present specification, the components of the vascular function extraction apparatus 100 will be described in detail through a process of a vascular function extracting method (S100) performed by the vascular function extraction apparatus 100.

Figure 2:
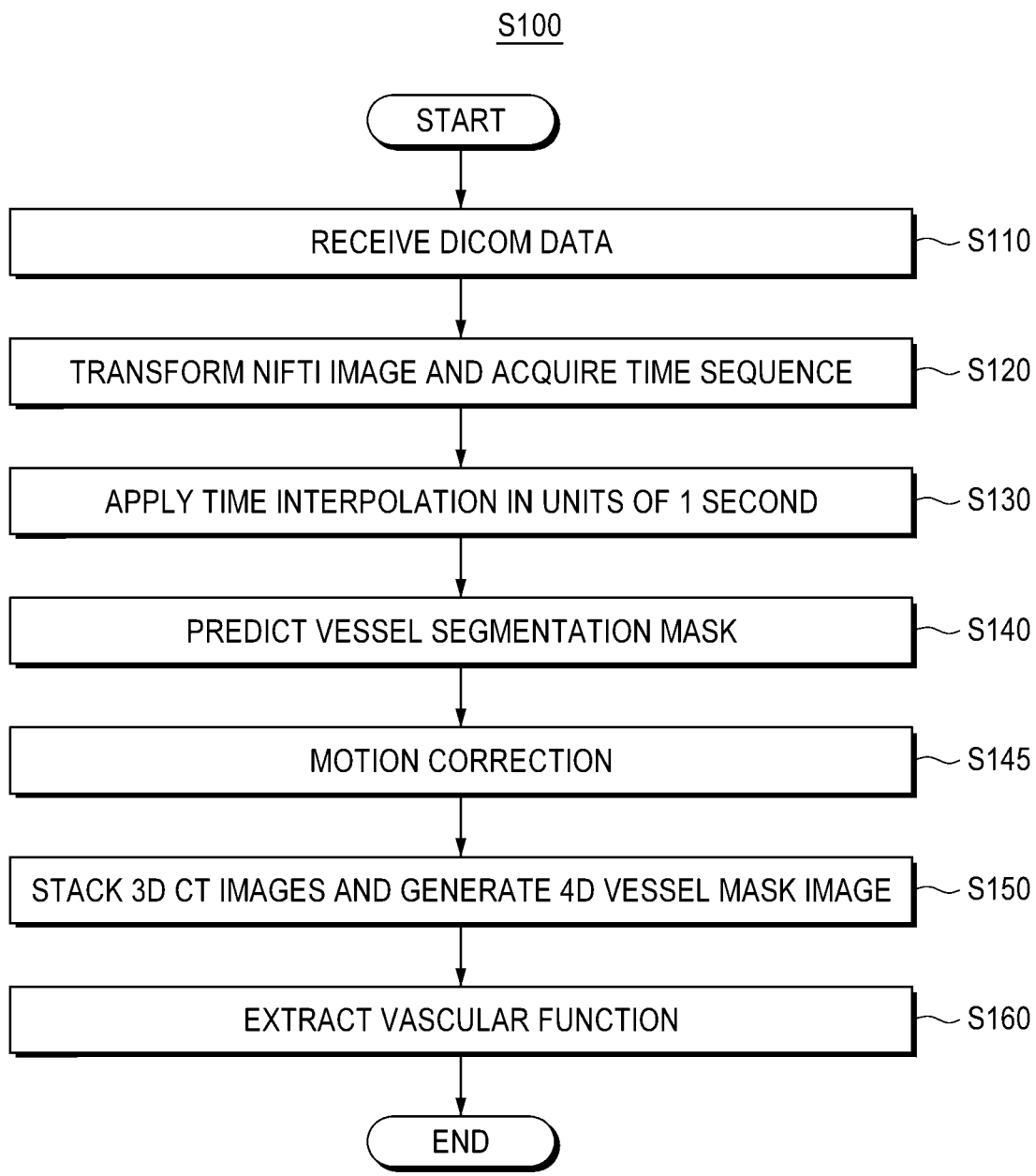
FIG. 2 illustrates an example of a method for extracting a vascular function performed by the vascular function apparatus described in FIG. 1.

The process of the vascular function extracting method (S100), which is a method for accurately extracting the vascular function using the vascular function extraction apparatus 100, is as illustrated in FIG. 2.

FIG. 2 illustrates an example of a method for extracting a vascular function performed by the vascular function apparatus described in FIG. 1.

Referring to FIG. 2, the information reception unit 110 may receive brain-related information from the outside (S110).

At this time, the brain-related information received by the information reception unit 110 is data conforming to a standard format in the field of medical imaging (Digital Imaging and Communications in Medicine, DICOM), and may include a CT image and a cerebrovascular map.

In the present specification, brain-related information and Dicom data may be used interchangeably, and the two terms refer to the same meaning.

In addition, the CT image included in the Dicom data received by the information reception unit 110 may be a 3D raw CT image received by the head segmentation unit 10.

The information reception unit 110 may extract the original CT image and the cerebrovascular map from the received Dicom data, respectively, and information such as the cerebrovascular map and the like excluding the original CT image may be provided to the user.

That is, since the information reception unit 110 aims to extract the original CT image, the process of receiving the brain-related information from the outside may also be replaced with a process of receiving a CT image from external equipment, like the head segmentation unit 10 to be described below.

Referring to FIG. 2, when receiving an original CT image from the information reception unit 110, the NIFTI image transformation unit 120 may transform the received original CT image into a neuroimaging informatics technology initiative (NIFTI) file format image (S120).

In addition, the NIFTI image transformation unit 120 transforms the original CT image into an NIFTI file format image, thereby acquiring a time sequence.

Referring to FIG. 2, when the time interpolation unit 130 receives data of the original CT image transformed into the NIFTI file format image and the time sequence from the NIFTI image transformation unit 120, the time interpolation unit 130 may apply time interpolation to the original CT image transformed into the received NIFTI file format image (S130).

At this time, the original CT image may be applied with time interpolation in units of 1 second from the time interpolation unit 130, and as a result, may be transformed into a 3D CT image D for each time in units of 1 second.

In the present specification, the 3D CT image D may be a 3D image of Slice×Height×Width.

Referring to FIG. 2, when receiving the 3D image D from the time interpolation unit 130, the vessel segmentation unit 140 may transform the received 3D CT image D into a 4D CT perfusion (CTP) image, and acquire a vessel segmentation mask of the 4D CTP image.

A step of acquiring a vessel segmentation mask of a 4D CTP image by the vessel segmentation unit 140 will be described in detail with reference to FIG. 3.

Figure 3:
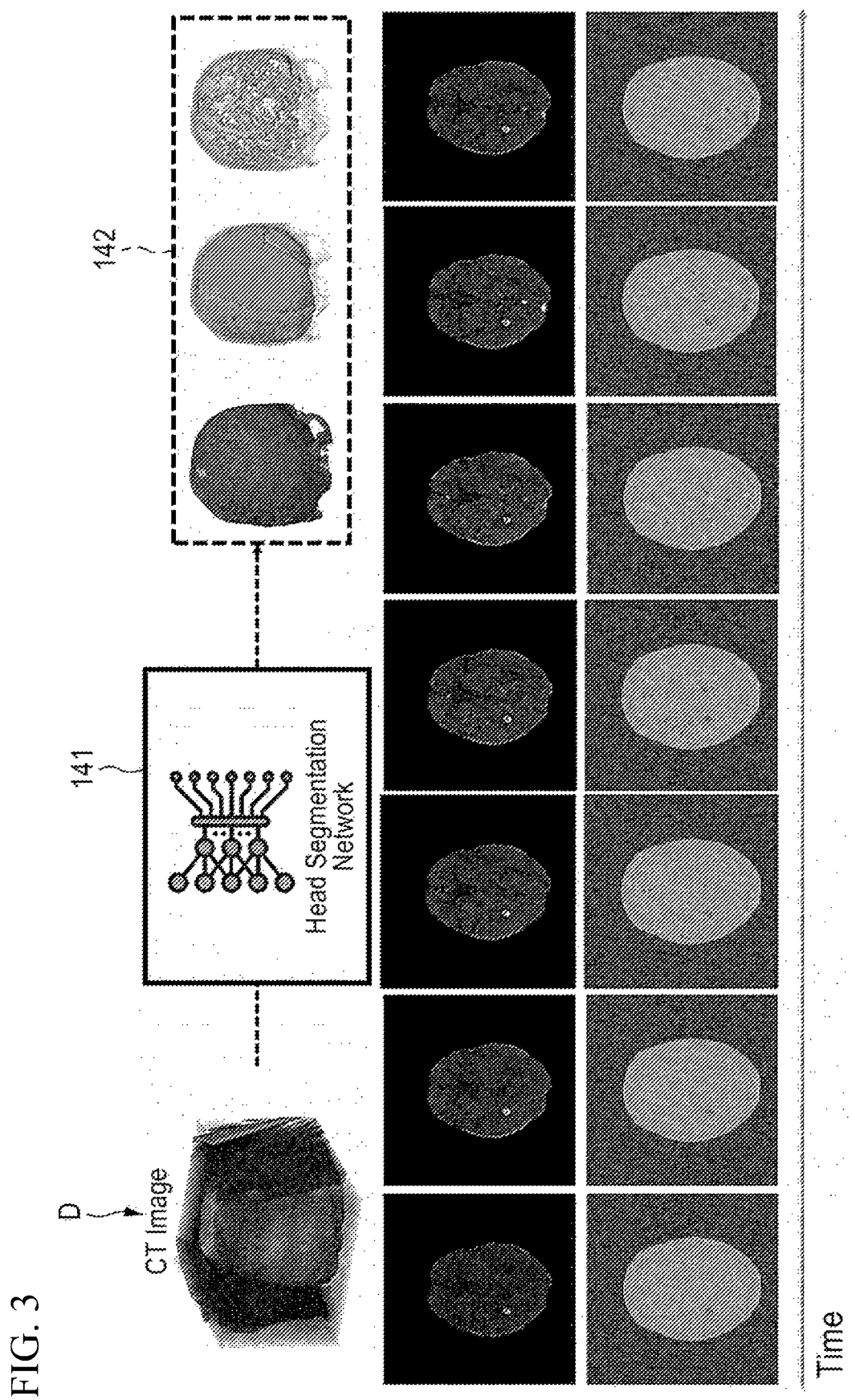
FIG. 3 is a diagram illustrating a vessel segmentation method in a vessel segmentation step described in FIG. 2.

FIG. 3 is a diagram describing a vessel segmentation method in the vessel segmentation step described in FIG. 2.

Referring to FIG. 3, in order to acquire a vessel segmentation mask from a 4D CT perfusion (CTP) image, when receiving the 3D CT image D from the time interpolation unit 130, the vessel segmentation unit 140 may predict (or acquire) a vessel segmentation mask by passing the 3D CT image D for each time through a deep learning-based vessel segmentation deep-learning model 141 (S140).

In this case, the deep learning-based vessel segmentation deep-learning model 141 may be a deep learning model that has been learned and verified in the same manner as a head segmentation network configured in the head segmentation unit 10 to be described below, only with a different reference number.

In addition, the mask predicted by the vessel segmentation deep-learning model 141 may be a vessel segmentation mask including at least two or more of a bone mask, a brain mask, a tissue mask, a vein mask, an artery mask, and the like.

The artery mask predicted by the vessel segmentation deep-learning model 141 may be used to extract an artery function, and the vein mask may be used to extract a vein function.

The vessel segmentation unit 140 may generate a 4D vessel mask image by predicting (or acquiring) a vessel segmentation mask and then stacking the 3D CT images D based on a time axis (S150).

In the present specification, the 4D vessel mask image and the 4D CTP image may be used interchangeably, and the two terms have the same meaning.

In the present specification, the 4D vessel mask image may be a 4D image of time×Slice×Height×Width which is generated by stacking the 3D CT images D.

In addition, as described above, the vessel segmentation unit 140 segments bone, brain, tissue, vein, artery, etc. with respect to each time axis of the 4D CTP image, and then sets a region of interest of the brain region in the entire phase to set one volume of interest (VOI) for the brain.

Referring back to FIG. 2, the motion correction unit 150 may perform the motion correction of the 3D CT images D (S145), between a step (S140) of predicting the mask by passing the 3D CT images D for each time of the vessel segmentation unit 140 through the deep learning-based vessel segmentation deep-learning model 141 and a step (S150) of stacking the 3D CT images D based on the time axis.

The motion correction step (S145) of the motion correction unit 150 is not necessarily limited to be performed, and the process may also be omitted according to settings set by the user of the apparatus 100.

Figure 4:
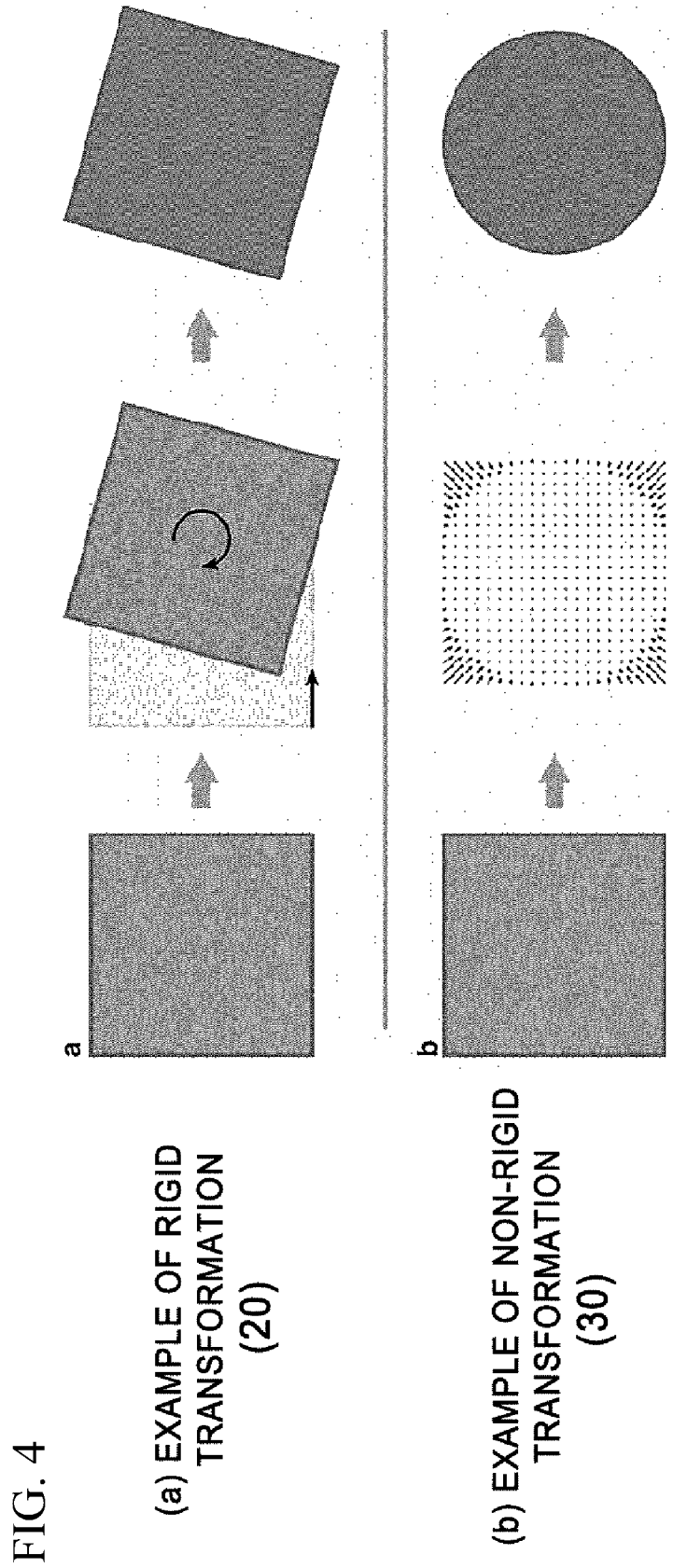
FIG. 4 is a diagram illustrating a motion correction concept of a motion correction unit according to an exemplary embodiment of the present disclosure.
Figure 5:
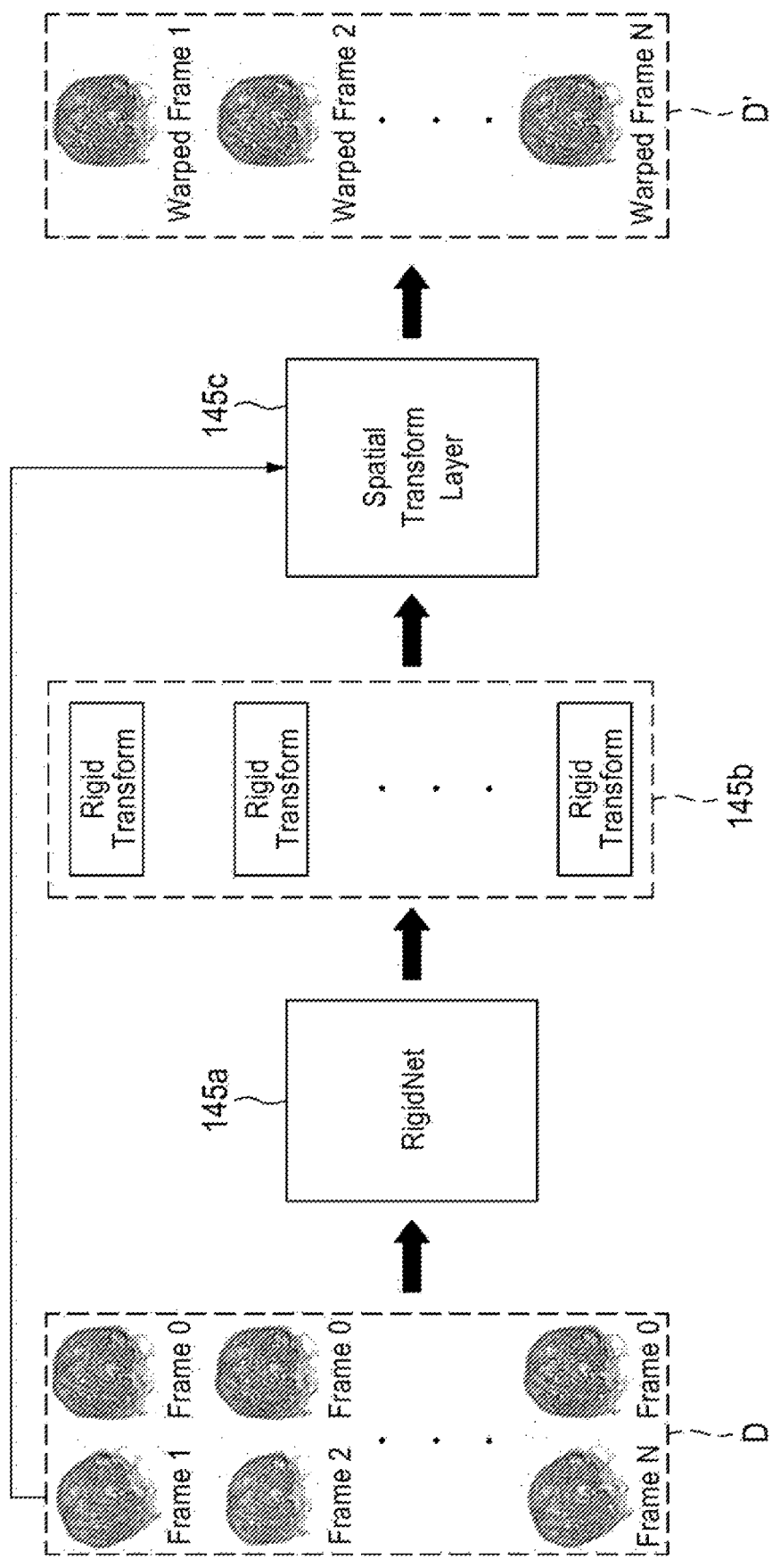
FIG. 5 illustrates an example of the motion correction step described in FIG. 2.

In one exemplary embodiment, drawings for describing the motion correction step (S145) of the motion correction unit 150 are as illustrated in FIGS. 4 and 5.

FIG. 4 is a diagram illustrating a motion correction concept of the motion correction unit according to an exemplary embodiment of the present disclosure.

When the patient's head moves even slightly while capturing a 3D CT image D of a patient based on a time axis, it is difficult to accurately detect artery and vein functions, and accordingly, it is difficult to accurately calculate blood flow parameters.

At this time, based on a 3D CT image D of a 0-th frame, as illustrated in FIG. 4, a 3D CT image D of a specific frame distorted due to a patient's motion needs to be applied with a rigid transformation 145b for the 3D CT image D of the 0-th frame.

Here, the rigid transformation is called a Euclidean transformation, and means a transformation in which only a location and a direction are changed while maintaining the shape and the size thereof.

In the present specification, the motion correction unit 150 may predict the rigid transformation 145b for the 3D CT image D of the 0-th frame with respect to 3D CT images D of frames other than the 0-th frame, and then apply an inverse transform to correct the motion of the 3D CT image D by matching the 3D CT images D of the remaining frames with the 3D CT image D of the 0-th frame. As such, an example of the motion correction step (S145) of correcting the motion of the 3D CT image D is as illustrated in FIG. 5.

FIG. 5 illustrates an example of the motion correction step described in FIG. 2.

Referring to FIG. 5, in the motion correction step (S145), the motion correction unit 150 inputs a 3D CT image D of each of frames 1 to N in addition to the 3D CT image D of the 0-th frame into a RigidNet 145a, which is an artificial intelligence model, acquires a rigid transformation 145b to calculate an inverse transformation, and then applies the inverse transformation to the 3D CT images D of the frames 1 to N on a spatial transformation layer 145c, so that the motion correction is applied to acquire 3D CT images D' of correction frames 1 to N matched with the 3D CT image D of the 0-th frame.

In one exemplary embodiment, the vessel segmentation unit 140 may generate a 4D vessel mask image by stacking the 3D CT image D of the 0-th frame to the 3D CT image D' of the correction frame N in the stacking step (S150).

Referring back to FIG. 2, when receiving the 4D vessel mask image from the vessel segmentation unit 140, the vascular function extraction unit 160 may extract the vascular function from a graph extracted from a vascular region of the received 4D vessel mask image, and then accurately extract a vascular function by correcting an inaccurate artery function included in the vascular function (S160).

The artery and vein function extraction step (S160) of the vascular function extraction unit 160 will be described in detail with reference to FIGS. 6 to 8.

Figure 6A:
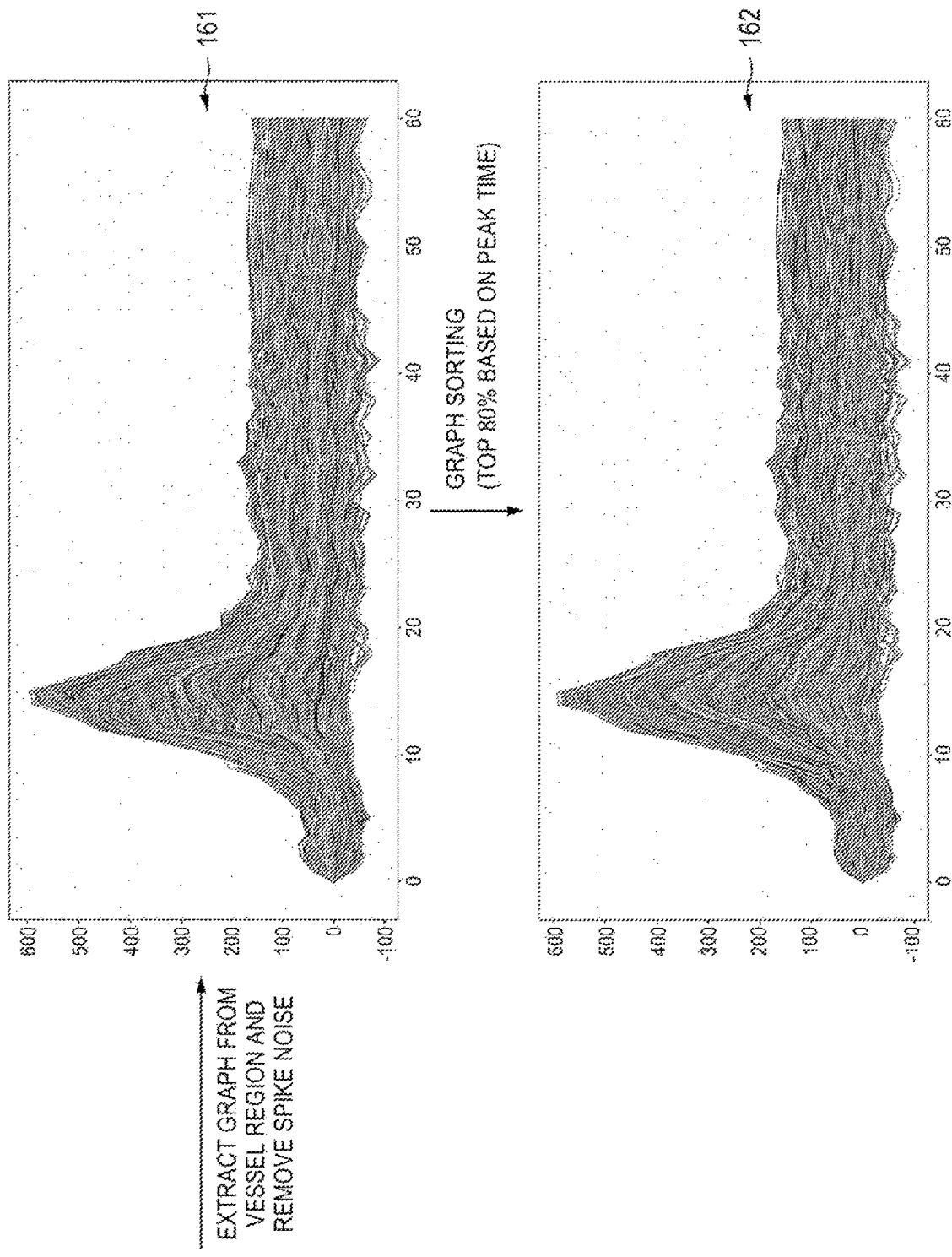
FIGS. 6A to 6C are diagrams illustrating a method for extracting artery and vein functions in a step of extracting artery and vein functions described in FIG. 2.
Figure 6B:
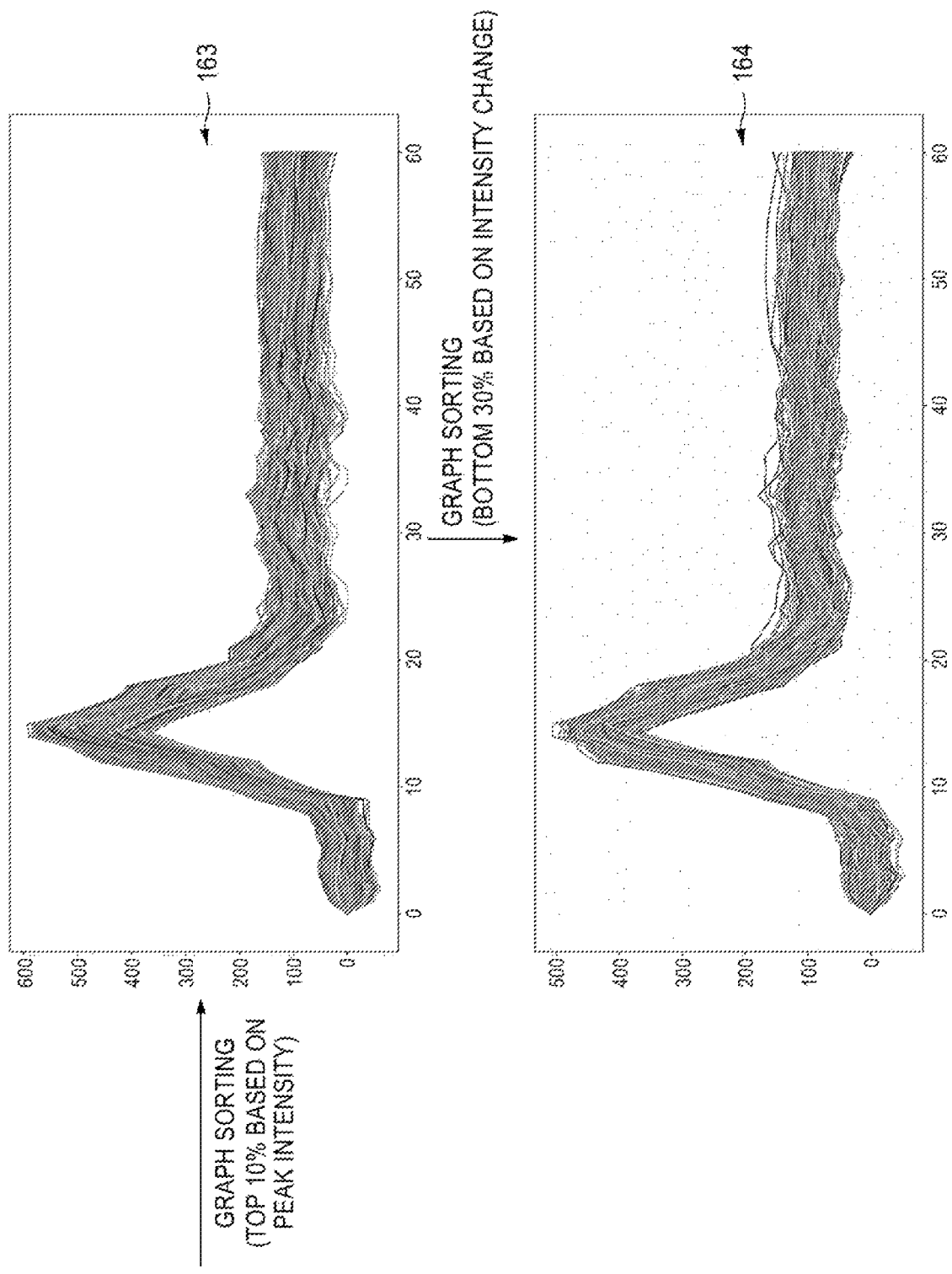
Figure 6C:
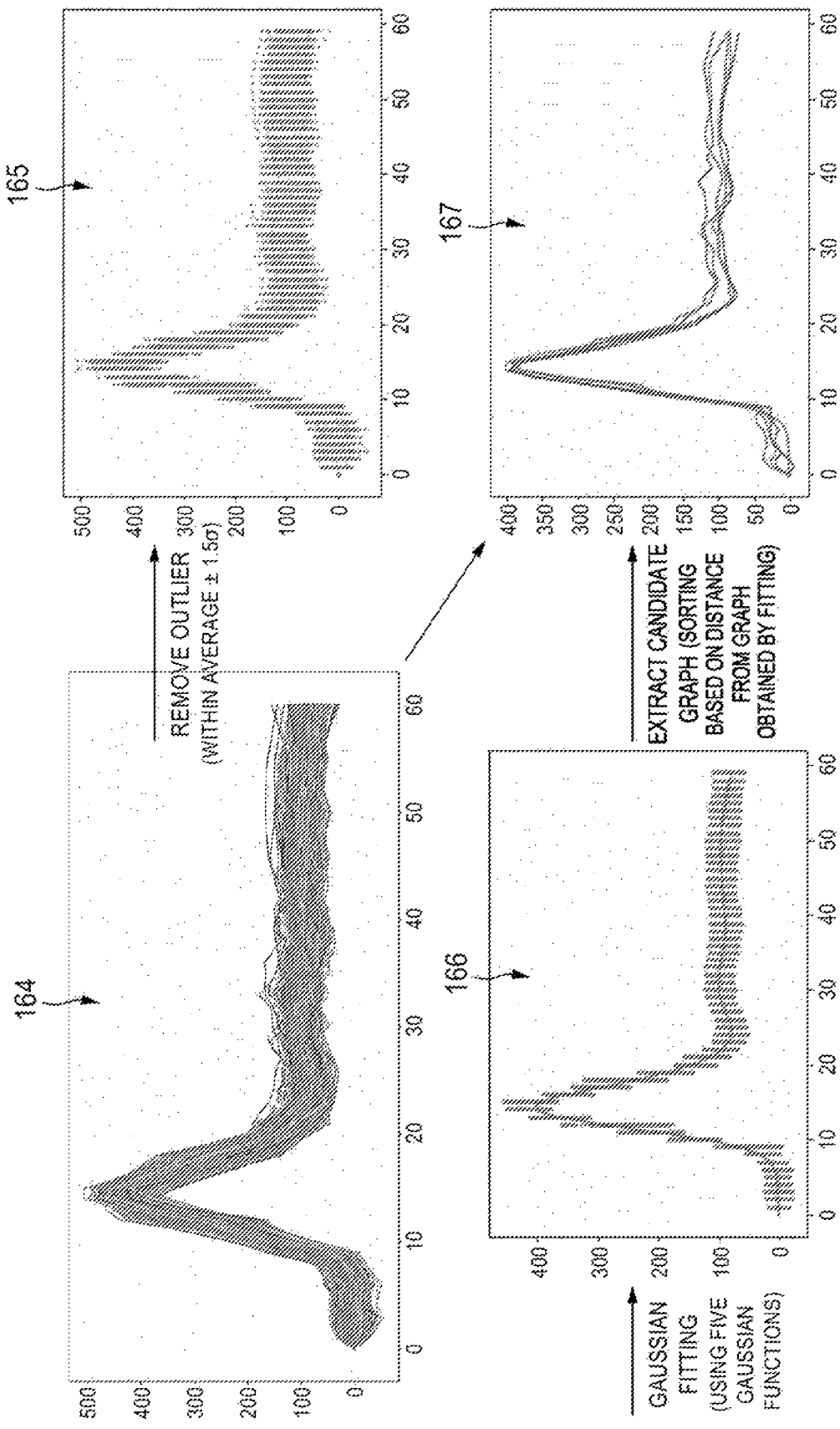
Figure 7:
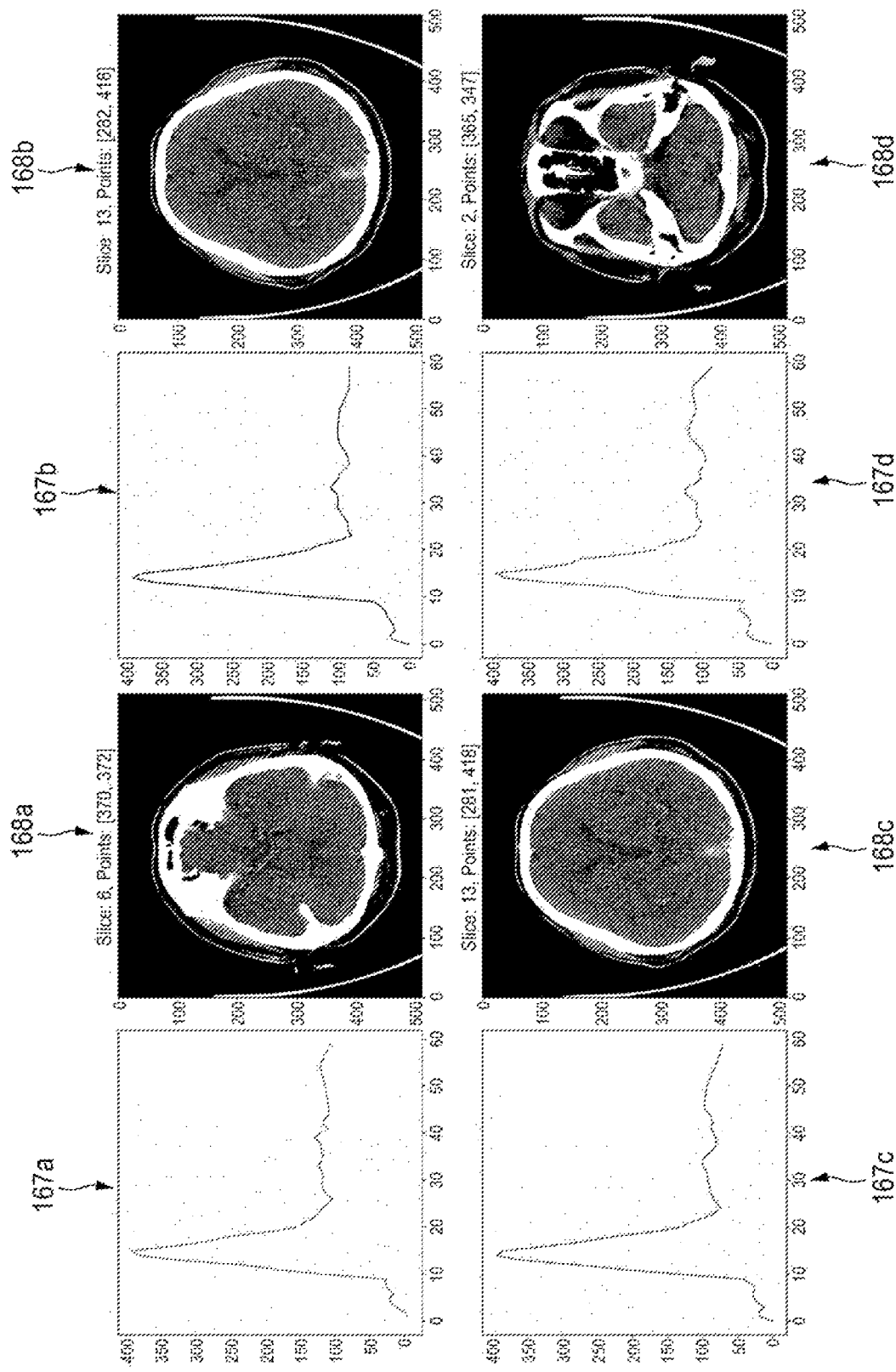
FIG. 7 illustrates examples of points and images corresponding to candidate graphs described in FIG. 6.
Figure 8:
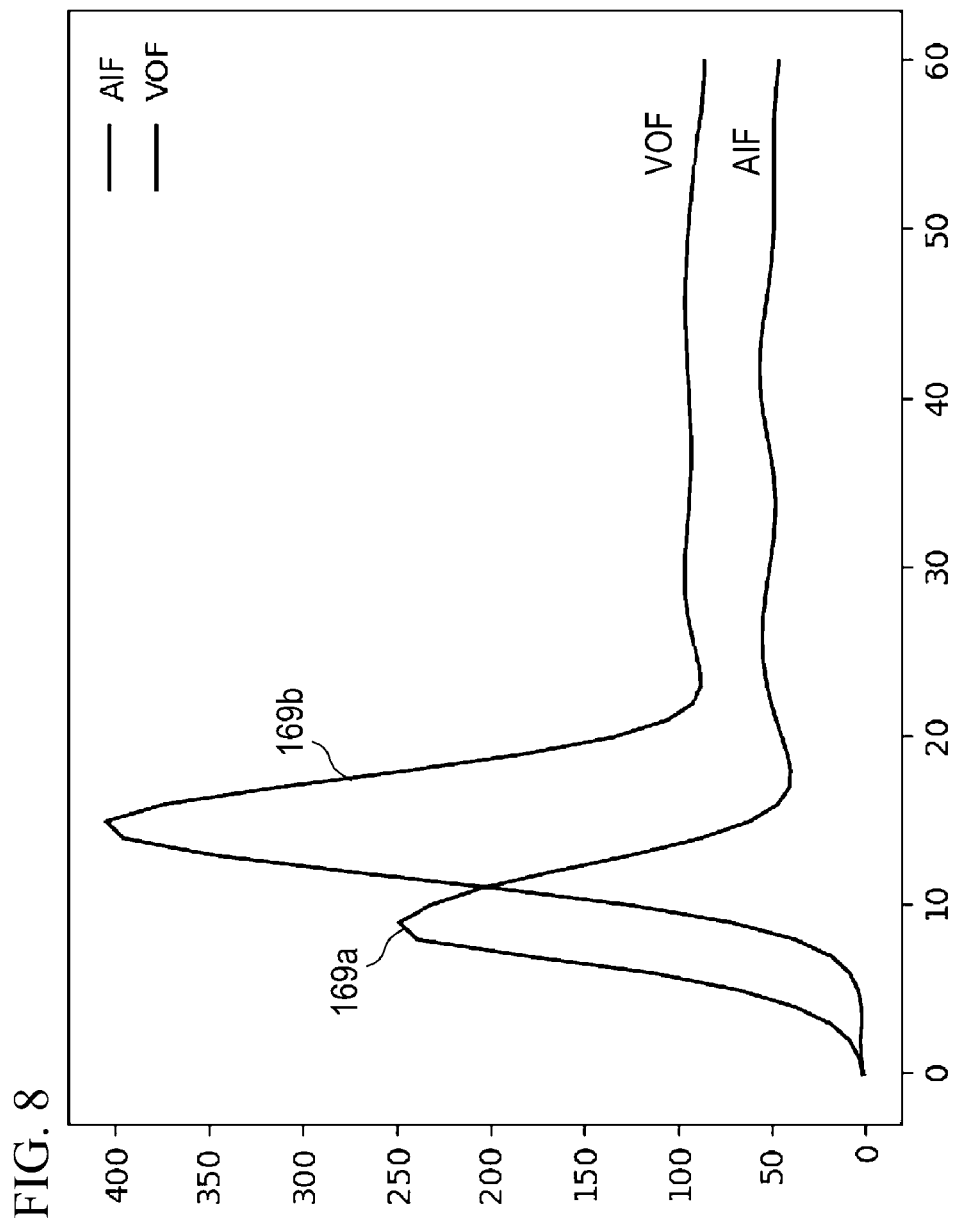
FIG. 8 illustrates an example of artery and vein functions extracted based on a graph extraction method in a vascular function extraction step described in FIG. 6.

FIGS. 6A to 6C are diagrams illustrating a method for extracting artery and vein functions in a step of extracting artery and vein functions described in FIG. 2, FIG. 7 illustrates examples of points and images corresponding to candidate graphs described in FIG. 6, and FIG. 8 illustrates an example of artery and vein functions extracted based on a graph extraction method in the artery and vein function extraction step described in FIG. 6.

Referring to FIG. 6A, when receiving the 4D vessel mask image from the vessel segmentation unit 140, the vascular function extraction unit 160 may generate a first graph 161 based on the highest intensity value in a time-specific phase corresponding to a pixel point (Slice, Height, Width coordinates) of each vessel in the vessel region of the received 4D vessel mask image.

In this case, the vascular function extraction unit 160 may remove spike noise, which is noise different from a pixel having normal luminance, in the process of generating the first graph 161.

After generating the first graph 161, the vascular function extraction unit 160 may generate a second graph 162 by sorting the intensity of the first graph 161.

At this time, a generation reference of the second graph 162 is not limited, but in the present specification, the second graph 162 may be a graph of the top 70 to 90% (preferably, 80%) based on the order in which the intensity reaches a peak fastest in the first graph 161.

Referring to FIG. 6B, after generating the second graph 162, the vascular function extraction unit 160 may generate a third graph 163 based on the order of increasing intensity values of peak points from the second graph 162.

At this time, a generation reference of the third graph 163 is not limited, but in the present specification, the third graph 163 may be a graph of the top 10 to 20% (preferably, 10%) based on the order of increasing the intensity value of the peak point of the second graph 162.

After generating the third graph 163, the vascular function extraction unit 160 may generate a fourth graph 164 based on the sum of changes in intensity for each time point of the third graph 163.

At this time, a generation reference of the fourth graph 164 is not limited, but in the present specification, the fourth graph 164 may be a graph of the bottom 20 to 40% (preferably, 30%) based on the order of increasing the sum of changes in intensity for each time point of the third graph 163.

Referring to FIG. 6C, after generating the fourth graph 164, the vascular function extraction unit 160 may calculate an average of intensities based on a time axis in the fourth graph 164, and generate a fifth graph 165, for example, by assuming points outside the range of average ±1 to 3σ (preferably, 1.5σ) as outliers and removing the points.

After generating the fifth graph 165, the vascular function extraction unit 160 may generate a sixth graph 166 by performing Gaussian fitting on the remaining points of the fifth graph 165.

At this time, the method for performing Gaussian fitting by the vascular function extraction unit 160 is not limited, but in the present specification, Gaussian fitting may be performed based on a plurality of (e.g., five) Gaussian functions.

The vascular function extraction unit 160 may extract a plurality of graphs having the closest distance to the sixth graph 166 from the fourth graph 164, simultaneously with the aforementioned Gaussian fitting process.

Thereafter, the vascular function extraction unit 160 may generate a candidate graph 167 based on a plurality of graphs having the closest distance to the sixth graph 166 from the sixth graph 166 and the fourth graph 164 acquired based on Gaussian fitting.

At this time, the generating of the candidate graph 167 is to allow a user of the apparatus 100 to delete a graph to be removed from among the candidate graphs 167 generated by the vascular function extraction unit 160 or to additionally include a graph not included in the candidate graphs 167.

Examples of first, second, third, and fourth points 167*a*, 167*b*, 167*c*, and 167*d* corresponding to the graphs of the candidate graphs 167 generated by the vascular function extraction unit 160 and first, second, third, and fourth images 168*a*, 168*b*, 168*c*, and 168*d* corresponding thereto are as illustrated in FIG. 6, respectively.

As such, the points 167*a* to 167*d* illustrated in FIG. 7 may include Slice coordinates, Height coordinates, and Width coordinates.

Meanwhile, as illustrated in FIG. 8, an artery function graph 169*a* and a vein function graph 169*b* may be applied in the same manner as the process of generating the candidate graph 167 from the aforementioned first graph 161 to be generated by the vascular function extraction unit 160.

At this time, the generating of the artery function graph 169*a* based on the process of generating the candidate graph 167 from the first graph 161 by the vascular function extraction unit 160 is to correct an inaccurate artery function based on a process of adding or deleting a graph for generating the candidate graph 167.

As such, the vascular function extraction unit 160 may correct an inaccurate artery function by adding or deleting the artery function graph 169*a*, and correct the inaccurate artery function to accurately calculate blood flow parameters such as CBV, MTT, and CBF that are calculated based on accurately corrected arterial function variables.

In one exemplary embodiment, the vascular function extraction unit 160 may configure a blood flow parameter model for accurately calculating blood flow parameters.

Blood Flow Parameter Model

A method for implementing the blood flow parameter model of the vascular function extraction 160 is as follows.

First, the blood flow parameter model of the vascular function extraction unit 160 may be learned to calculate blood flow parameters through a singular value decomposition (SVD)-based approach, which is a technique of separating a high-dimensional matrix into a low-dimensional matrix as one of matrix decomposition methods.

The blood flow parameter model of the vascular function extraction unit 160 may calculate a cerebral blood volume (CBV), which is one of the blood flow parameters, through [Equation 1] below.

$$CBV = \frac{\int C_v(t)dt}{\int C_a(t)} \quad \text{[Equation 1]}$$

In Equation 1, $C_v$ may be a concentration change of VOI tissue, and $C_a$ may be an artery function 159*a*.

As such, in order to calculate CBV, which is one of the blood flow parameters, the artery function 159*a* is applied as a variable, and in order to accurately calculate CBV, a process of correcting the inaccurate artery function 159*a* is required.

The blood flow parameter model of the vascular function extraction unit 160 may calculate mean transit time (MTT), which is one of the blood flow parameters, through [Equation 2] below.

$$MTT = \frac{CBV}{F_v} \quad \text{[Equation 2]}$$

In Equation 2, $F_v$ may be cerebral blood flow (CBF) as another blood flow parameter.

Meanwhile, an example of Equation for performing singular value decomposition by the blood flow parameter model of the vascular function extraction unit 160 is as shown in [Equation 3] below.

$$C_v(t_j) = \Delta t \cdot F_v \sum_{i=0}^{j} C_a(t_i) R(t_j - t_i), \quad \text{[Equation 3]}$$

In Equation 3, R is a residual function, and $C_a$ and $C_v$ may be normalized to a value of 0 at t=0.

Equations for decomposing a matrix by the blood flow parameter model of the vascular function extraction unit 160 through the SVD-based approach based on the formula of Equation 3 are as follows [Equation 4] to [Equation 8].

$$\begin{bmatrix} C_v(t_0) \\ C_v(t_1) \\ \vdots \\ C_v(t_{N-1}) \end{bmatrix} = \Delta t \begin{bmatrix} C_a(t_0) & 0 & \cdots & 0 \\ C_a(t_1) & C_a(t_0) & \cdots & 0 \\ \vdots & \vdots & \ddots & \vdots \\ C_a(t_{N-1}) & C_a(t_{N-2}) & \cdots & C_a(t_0) \end{bmatrix} \times \begin{bmatrix} R(t_0) \\ R(t_1) \\ \vdots \\ R(t_{N-1}) \end{bmatrix} \cdot F_v \quad \text{[Equation 4]}$$

$$C = Ar \quad \text{[Equation 5]}$$

$$A = USV^T \quad \text{[Equation 6]}$$

$$A^{-1} = VWU^T \quad \text{[Equation 7]}$$

$$r = A^{-1}C = VWU^T C \quad \text{[Equation 8]}$$

The blood flow parameter model of the vascular function extraction unit 160 may find a basis robust to noise by applying a threshold to a W term of Equation 7 above, which is a diagonal matrix.

Calculation of Blood Flow Parameters

The blood flow parameter model of the vascular function extraction unit 160 learned through an SVD-based approach may calculate the blood flow parameters CBF, CBV, and MTT, but a relationship between the blood flow parameters is as follows [Equation 9] to [Equation 11].

$$CBF = \frac{1}{\rho}\max(r'(t)) \quad \text{[Equation 9]}$$

$$CBV = \frac{1}{\rho}\frac{\int C(t)}{\int C_a(t)} \approx \frac{1}{\rho}\int r'(t) = CBF * MTT \quad \text{[Equation 10]}$$

$$MTT = \int \tau r(\tau)d\tau = CBV/CBF \quad \text{[Equation 11]}$$

The blood flow parameter model of the vascular function extraction unit 160 may calculate the blood flow parameters CBF, CBV, and MTT based on a r' value approximated so that a relationship between the blood flow parameters CBF, CBV, and MTT is established.

In this case, conditions for calculating the blood flow parameters CBF, CBV, and MTT may be 1.04 g/ml of an average brain density, #ml/100 g/min of a unit of CBF, and ml/100 g of a unit of CBV.

In addition, the 4D CTP image may be reconstructed into a 1 mm isotropic voxel.

When the units of the blood flow parameter model of the vascular function extraction unit 160 are adjusted as the condition, 100 g/1.04 is applied as a 1/p value, and when plotting CBF, the blood flow parameter calculated by multiplying 60 s based on minute (min) may be indicated.

Front-End Configuration of Apparatus for Extracting Vascular Function

The head segmentation unit 10 may be provided at the front end of the vascular function extracting apparatus 100 of the present disclosure.

The head segmentation unit 10 may receive a CT image and pass the CT image through a head segmentation network capable of dividing the skull and the brain to predict a bone mask of the skull, a brain mask of the brain, and a brain-related vessel mask.

In addition, the head segmentation unit 10 may extract a brain image including only a brain region from the CT image by combining the predicted brain mask and vessel mask.

Head Segmentation Unit

Figure 9:
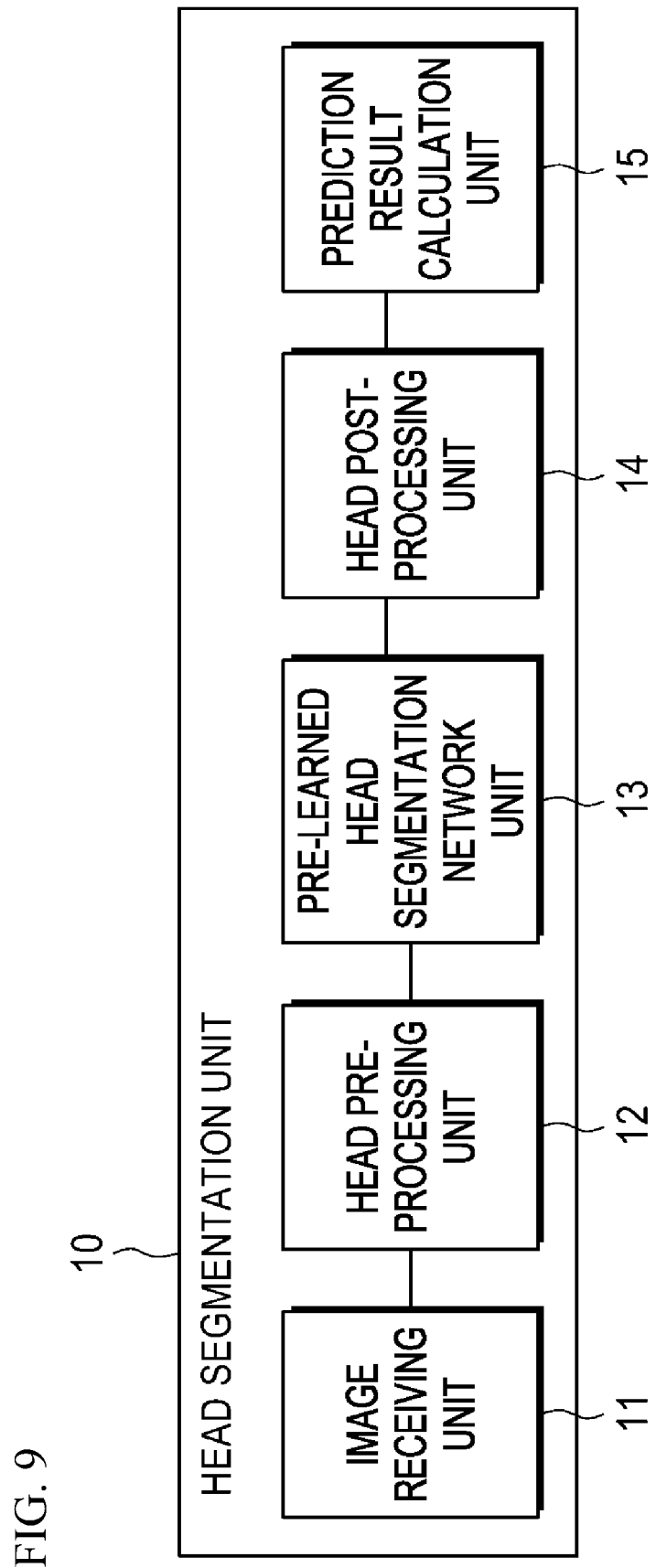
FIG. 9 illustrates an example of a block diagram of a head segmentation unit.

FIG. 9 shows an example of a block diagram of a head segmentation unit.

Referring to FIG. 9, the head segmentation unit 10 may include an image receiving unit 11, a head pre-processing unit 12, a pre-learned head segmentation network unit 13, a head post-processing unit 14, and a prediction result calculation unit 15.

Since a region of interest to be analyzed by the present disclosure is the brain, and the thickness and shape of the skull vary from person to person, the head segmentation unit 10 may perform an operation of predicting each bone, brain, and vessel mask by passing through a deep learning-based head segmentation network capable of dividing the skull and brain regions and then extracting a whole brain region from the original CT image by combining the brain mask and the vessel mask.

First, the image receiving unit 11 receives a CT image from external equipment.

Next, the head pre-processing unit 12 segments a 3D image of a raw CT image into 2D axial slices, and then concatenates adjacent slices to a slice to be segmented to constitute input data.

Specifically, the input data is input to the pre-learned head segmentation network unit 13 through the pre-processing of the head pre-processing unit 12.

The head pre-processing unit 12 may perform operations such as (1) resizing, (2) HU windowing, (3) normalizing, and the like.

(1) The resizing operation is an operation of reducing and/or enlarging an image to a size required by the head segmentation network.

Next, the (2) HU windowing operation is an operation of setting the upper and lower limits of a Hounsfield unit (HU).

In addition, the normalizing operation is an operation of determining a HU Level from the set lower limit to an upper limit, and mapping the HU Level at a determined [0, 1] interval. Representatively, a method of mapping the HU Level from the lower limit to the upper limit of HU windowing at an interval of [0, 1] may be applied.

The pre-processed CT image passes through the pre-learned head segmentation network unit 13, and with respect to the CT image passing through the head segmentation network unit 13, the head post-processing unit 14 performs post-processing, which is at least one of a brain VOI crop operation and an outlier cluster removing operation.

The pre-learned head segmentation network unit 13 is a deep learning-based segmentation network pre-learned for skull and brain regions so as to extract a brain region, which is a region of interest.

Here, the brain VOI crop operation is an operation of resizing after removing a region other than a volume region of interest for the brain.

In addition, the outlier cluster removing operation is an operation of removing a small outlier cluster that is not connected but separated in a three dimension.

Thereafter, the prediction result calculation unit predicts the bone mask, the brain mask, and the vessel mask based on the post-processed CT image.

That is, the prediction result calculation unit 15 may predict the bone mask of the skull, the brain mask of the brain, and the brain-related vessel mask, and extract a brain image including only a brain region from a first input CT image by combining the predicted brain mask and vessel mask.

Operation of Head Segmentation Unit

Figure 10:
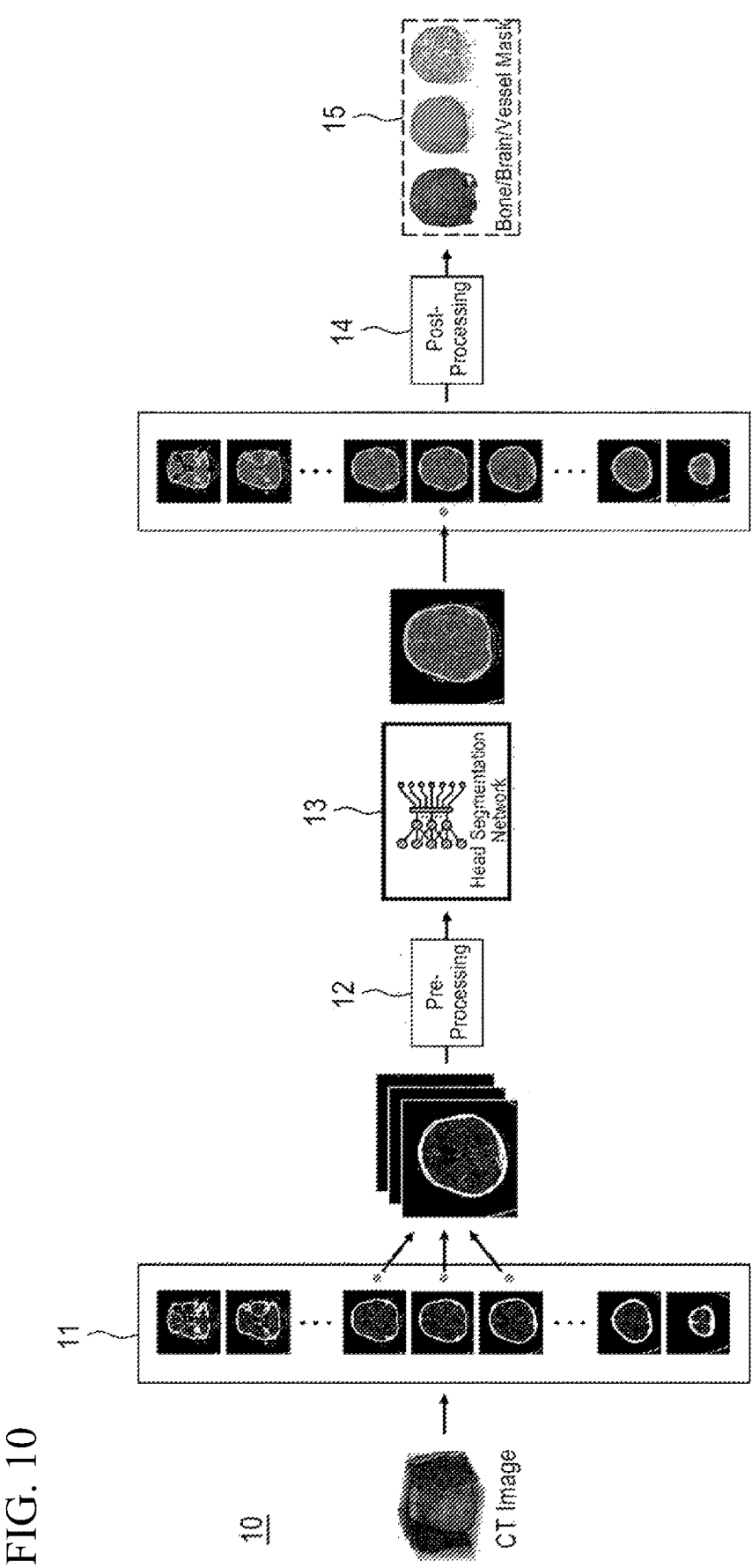
FIG. 10 illustrates an operation of the head segmentation unit described in FIG. 9 over time.

FIG. 10 illustrates an operation of the head segmentation unit described in FIG. 9 over time.

Referring to FIG. 10, the image receiving unit 11 receives a CT image from external equipment.

Next, the head pre-processing unit 12 segments a 3D image of a raw CT image into 2D axial slices, and then concatenates adjacent slices to a slice to be segmented to constitute input data.

Specifically, the input data is input to the pre-learned head segmentation network unit 13 through the pre-processing of the head pre-processing unit 12.

The head pre-processing unit 12 may perform operations such as (1) resizing, (2) HU windowing, (3) normalizing, and the like.

The pre-processed CT image passes through the pre-learned head segmentation network unit 13, and with respect to the CT image passing through the head segmentation network unit 13, the head post-processing unit 14 performs post-processing, which is at least one of a brain VOI crop operation and an outlier cluster removing operation.

Thereafter, the prediction result calculation unit predicts information 15 including a bone mask 17, a brain mask 18, and a vessel mask 19 based on the post-processed CT image.

That is, the prediction result calculation unit 15 may predict the bone mask 17 of the skull, the brain mask 18 of the brain, and the brain-related vessel mask 19, and extract a brain image K including only a brain region from a first input CT image by combining the predicted brain mask 18 and vessel mask 19.

Effects Provided by the Present Disclosure

According to the present disclosure, it is possible to provide a user with an apparatus and a method for extracting a vascular function from brain-related information.

Specifically, according to the present disclosure, it is possible to provide a user with an apparatus and a method for extracting a vascular function from brain-related information by extracting a vascular function from brain-related information generated based on an original CT image and then correcting an inaccurate artery function to acquire an accurate artery function, in order to accurately calculate blood flow parameters such as CBV, MTT, and CBF.

A technical object to be achieved in the present disclosure is not limited to the aforementioned effects, and another not-mentioned effect will be obviously understood by those skilled in the art from the description below.

The above-described exemplary embodiments of the present disclosure may be implemented through various methods. For example, the exemplary embodiments of the present disclosure may be implemented by a hardware, a firmware, a software, or a combination thereof.

When the exemplary embodiment is implemented by the hardware, the method according to the exemplary embodiment of the present disclosure may be implemented by one or more application specific integrated circuits (ASICs), digital signal processors (DSPs), digital signal processing devices (DSPDs), programmable logic devices (PLDs), field programmable gate arrays (FPGAs), a processor, a controller, a microcontroller, or a microprocessor.

When the exemplary embodiment is implemented by the firmware or the software, the method according to the exemplary embodiment of the present disclosure may be implemented by a module, a procedure, or a function which performs a function or operations described above. The software code is stored in the memory unit to be driven by the processor. The memory unit is located inside or outside the processor and may exchange data with the processor, by various known units.

As described above, the detailed description of the preferred exemplary embodiments of the disclosed present disclosure is provided such that those skilled in the art implement and carry out the present disclosure. While the present disclosure has been described with reference to the preferred exemplary embodiments, it will be understood by those skilled in the art that various changes and modifications of the present disclosure may be made without departing from the scope of the present disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be implemented in another specific form within the scope without departing from the spirit and essential feature of the present disclosure. Therefore, the detailed description should not restrictively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the exemplary embodiment or may be included as new claims by correction after filing.

What is claimed is:

1. An apparatus for extracting a vascular function from brain-related information comprising:
    an information reception unit configured to extract an original CT image from the brain-related information received from the outside;
    an NIFTI image transformation unit configured to transform the original CT image into a neuroimaging informatics technology initiative (NIFTI) file format image to acquire time sequence data;
    a time interpolation unit configured to apply time interpolation to the original CT image through the time sequence data to transform the original CT image into each time-specific 3D CT image;
    a vessel segmentation unit configured to predict a vessel segmentation mask by passing the each time-specific 3D CT image through a deep learning-based vessel segmentation deep-learning model and generate a 4D vessel mask image by stacking the 3D CT images based on a time axis; and
    a vascular function extraction unit configured to extract a vascular function from a vessel region of the 4D vessel mask image and calculate a blood flow parameter using an artery function which is one of the vascular functions.

2. The apparatus for extracting the vascular function from brain-related information of claim 1, further comprising:
    a motion correction unit configured to correct a motion of the each time-specific 3D CT image based on a rigid transformation, between the predicting of the vessel segmentation mask and the generating of the 4D vessel mask image by the vessel segmentation unit.

3. The apparatus for extracting the vascular function from brain-related information of claim 1, wherein the vessel segmentation unit acquires the vessel segmentation mask of the 4D vessel mask image including at least two or more of a bone mask, a brain mask, a tissue mask, a vein mask, and an artery mask, which are predicted by the vessel segmentation deep-learning model.

4. The apparatus for extracting the vascular function from brain-related information of claim 3, wherein the artery mask is used when the vascular function extraction unit extracts the artery function.

5. The apparatus for extracting the vascular function from brain-related information of claim 3, wherein the vein mask is used when the vascular function extraction unit extracts the vein function.

6. The apparatus for extracting the vascular function from brain-related information of claim 1, wherein the vascular function extraction unit generates a first graph based on a highest intensity value in a time-specific phase corresponding to a pixel point of each vessel corresponding to Slice, Height, and Width coordinates in the vessel region of the 4D vessel mask image.

7. The apparatus for extracting the vascular function from brain-related information of claim 6, wherein the vascular function extraction unit removes spike noise in the process of generating the first graph.

8. The apparatus for extracting the vascular function from brain-related information of claim 6, wherein the vascular function extraction unit generates a second graph by sorting the intensity of the first graph based on an order in which the intensity reaches a peak fastest in the first graph.

9. The apparatus for extracting the vascular function from brain-related information of claim 8, wherein the second graph is a graph of the top 70 to 90% based on the order in which the intensity reaches the peak fastest in the first graph.

10. The apparatus for extracting the vascular function from brain-related information of claim 8, wherein the vascular function extraction unit generates a third graph based on the order of increasing intensity values of peak points from the second graph.

11. The apparatus for extracting the vascular function from brain-related information of claim 10, wherein the third graph is a graph of the top 10 to 20% based on the order of increasing the intensity value of the peak point of the second graph.

12. The apparatus for extracting the vascular function from brain-related information of claim 10, wherein the vascular function extraction unit generates a fourth graph based on a sum of changes in intensity for each time point of the third graph.

13. The apparatus for extracting the vascular function from brain-related information of claim 12, wherein the fourth graph is a graph of the bottom 20 to 40% based on the order of increasing the sum of changes in intensity for each time point of the third graph.

14. The apparatus for extracting the vascular function from brain-related information of claim 12, wherein the vascular function extraction unit calculates an average of intensities based on a time axis in the fourth graph, and generates a fifth graph by assuming points out of a predetermined range as outliers and removing the points.

15. The apparatus for extracting the vascular function from brain-related information of claim 14, wherein the fifth graph is a graph of removing the points out of a range of average ±1 to 3σ in the fourth graph as the outliers.

16. The apparatus for extracting the vascular function from brain-related information of claim 14, wherein the vascular function extraction unit generates a sixth graph by performing Gaussian fitting on the remaining points of the fifth graph.

17. The apparatus for extracting the vascular function from brain-related information of claim 16, wherein the vascular function extraction unit extracts a plurality of graphs having a closest distance to the sixth graph from the fourth graph, simultaneously with the Gaussian fitting process, and
generates a candidate graph based on the plurality of graphs and the sixth graph.

18. The apparatus for extracting the vascular function from brain-related information of claim 17, wherein the candidate graph is obtained by adding or deleting a graph by a user.

19. The apparatus for extracting the vascular function from brain-related information of claim 18, wherein the vascular function extraction unit extracts an artery function-based artery function graph based on the process of generating the candidate graph from the first graph, and
the artery function graph is obtained by correcting the artery function based on the process of adding or deleting graphs of the candidate graph.

20. The apparatus for extracting the vascular function from brain-related information of claim 19, wherein the vascular function extraction unit calculates blood flow parameters such as cerebral blood volume (CBV), mean transit time (MTT), and capillary blood flow (CBF) based on the corrected artery function.

21. The apparatus for extracting the vascular function from brain-related information of claim 1, wherein the time interpolation unit transforms the original CT image into each time-specific 3D CT image in units of 1 second by applying time interpolation in units of 1 second to the original CT image.

22. A method for extracting a vascular function from brain-related information comprising:
(a) extracting, by an information reception unit, an original CT image from brain-related information received from the outside;
(b) transforming, by an NIFTI image transformation unit, the original CT image into a neuroimaging informatics technology initiative (NIFTI) file format image to acquire time sequence data;
(c) applying, by a time interpolation unit, time interpolation to the original CT image through the time sequence data to transform the original CT image into each time-specific 3D CT image;
(d) predicting, by a vessel segmentation unit, a vessel segmentation mask by passing the each time-specific 3D CT image through a deep learning-based vessel segmentation deep-learning model and generating a 4D vessel mask image by stacking the 3D CT images based on a time axis; and
(e) extracting, by a vascular function extraction unit, a vascular function from a vessel region of the 4D vessel mask image and calculating a blood flow parameter using an artery function which is one of the vascular functions.

* * * * *